(12) United States Patent
Navarro et al.

(10) Patent No.: US 6,398,777 B1
(45) Date of Patent: Jun. 4, 2002

(54) ENDOVASCULAR LASER DEVICE AND TREATMENT OF VARICOSE VEINS

(76) Inventors: Luis Navarro, 164 E. 71st St., New York, NY (US) 10021; Nestor Navarro, Manuel Girona 74, Barcelona (ES), 08034; Carlos Bone Salat; Joaquina Fructuoso Gomez, both of Santa Lavinea, No. 7, Costa d'en Blane Calvia, Mallorca (ES), 07018; Robert J. Min, 2000 Broadway #8C, New York, NY (US) 10023

(*) Notice: Subject to any disclaimer, the term of this patent is extended or adjusted under 35 U.S.C. 154(b) by 0 days.

(21) Appl. No.: 09/374,280

(22) Filed: Aug. 13, 1999

(51) Int. Cl.[7] ............................................... A61B 18/18
(52) U.S. Cl. .............................. 606/7; 606/13; 606/14; 606/15; 607/89; 128/898
(58) Field of Search ..................... 606/13–15, 7, 606/8; 607/88, 89, 92–94; 128/898

(56) References Cited

U.S. PATENT DOCUMENTS

| | | | |
|---|---|---|---|
| 4,564,011 A | * | 1/1986 | Goldman ................. 128/303.1 |
| 4,587,972 A | | 5/1986 | Morantte, Jr. |
| 4,852,567 A | | 8/1989 | Sinofsky |
| 5,053,033 A | | 10/1991 | Clarke |
| 5,161,526 A | | 11/1992 | Hellwing et al. |
| 5,304,171 A | * | 4/1994 | Gregory et al. ............... 606/15 |
| 5,334,207 A | * | 8/1994 | Gay, Jr. ........................ 606/7 |
| 5,531,739 A | * | 7/1996 | Trelles ....................... 606/2.5 |
| 5,707,403 A | | 1/1998 | Grove et al. |
| 5,814,039 A | | 9/1998 | Prescott ........................ 606/7 |
| 5,840,008 A | | 11/1998 | Klein et al. .................... 600/3 |
| 5,855,563 A | | 1/1999 | Kaplan et al. ................ 604/49 |
| 5,984,915 A | * | 11/1999 | Leob et al. .................... 606/9 |

FOREIGN PATENT DOCUMENTS

ES  P9701586  7/1997

* cited by examiner

*Primary Examiner*—Linda C. M. Dvorak
*Assistant Examiner*—Ahmed Farah
(74) *Attorney, Agent, or Firm*—Steinberg & Raskin, P.C.

(57) ABSTRACT

A method is disclosed for treating blood vessels using endovascular techniques to deliver laser energy. Percutaneous access into the vein lumen will be obtained using an angiocatheter through which a fiber optic line will be introduced. The vein will be emptied of blood using elevation of the limb, patient positioning, compression, or other means. Laser energy will be delivered into the vein lumen using wavelengths from about 532 nanometers to about 1064 nanometers. Sufficient power and duration will be used to damage the entire thickness of the vein wall, ultimately causing fibrosis of the treated blood vessel. Fibrosis of the treated blood vessel causes the blood vessel to decrease in diameter or collapse.

21 Claims, 9 Drawing Sheets

ENDOVASCULAR LASER DEVICE AND TREATMENT OF VARICOSE VEINS

BACKGROUND OF THE INVENTION

1. Field of the Invention

The present invention relates to a method for treating varicose veins. More particularly, the present invention relates to a method of utilizing laser energy delivered into the vessel lumen via endovascular techniques to treat varicose veins.

2. Description of the Prior Art

The use of lasers in the treatment of vascular disease has been gaining rapid interest. Lesions such as port wine stains, facial telangiectasias, and some lower extremity veins have been treated externally by lasers with some success. Most of these laser procedures irradiate the surface of the skin with laser energy that penetrates the skin, is absorbed by the blood, and coagulates and collapses the blood vessel.

Larger varicose veins are located deeper in the soft tissues. Such veins have not been successfully treated with laser techniques. It is believed that treating such larger veins with laser energy delivered from the surface would require higher powers that could lead to increased side effects including scarring and skin hyper- or hypopigmentation.

Current accepted treatments of varicose veins include sclerotherapy, ambulatory phlebectomy, and ligation and stripping of the greater saphenous vein in cases of saphenofemoral junction incompetence. Although there has been wide variation in reported results of sclerotherapy treatment of the greater saphenous vein when saphenofemoral junction reflux is present, most studies report recurrence rates of 30% to 70% after 5 years. The existing standard for the treatment of saphenofemoral junction reflux is limited ligation and stripping of the greater saphenous vein.

The obvious drawbacks of traditional surgical therapy include the increased risks and costs associated with more extensive anesthesia because general anesthesia is normally used during varicose vein surgery, instead of local anesthesia. In addition, there are possible complications of the surgery that include bleeding, infection, hypertrophic scars, ankle paresthesia, and a prolonged recovery period. Ambulatory phlebectomy for treatment of saphenopopliteal junction reflux or isolated perforator incompetence is less invasive than ligation and stripping and can be done with local anesthesia. However, complications incident to the surgical procedure may still occur.

The search for less invasive techniques to treat varicose veins with acceptable short and long term results has led to the development of additional treatment modalities. These modalities include ultrasound guided sclerotherapy (echo sclerotherapy), monopolar electrocautery, and a bipolar radio frequency based energy source delivered by a disposable catheter (VNUS).

Although, perhaps more invasive than surface laser irradiation, there are potential advantages to delivering laser energy from below the skin. Such advantages include a decrease in thermal damage to intervening tissue and minimization of the possible side effects to the skin itself.

In Spanish Patent No. 9701586 to Salat et al., electricity is used to treat varicose veins. The Salat et al. patent describes an endoluminal electrocoagulator for varicose vein operations. The microsurgical instrument contemplated by that invention is essentially based on the use of an electrocoagulating microhead joined to a conductor wire with adequate flexibility to be inserted percutaneously. The use of electricity inevitably leads to coagulation of blood within the blood vessel rather than causing fibrosis of the blood vessel itself. However, it has now been found that fibrosis of the blood vessel is preferred because veins of a much larger diameter may therefore be treated safely and effectively.

In U.S. Pat. No. 4,564,011 to Goldman, laser energy is delivered from below the skin. The Goldman patent provides using laser energy delivered via a hollow needle insertable within a blood vessel to create a blood clot. The Goldman patent also provides using laser energy immediately adjacent to a damaged blood vessel for creating white scar tissue which tends to push against the vessel, thereby causing the vessel to shrink in size and at least partially disappear from view. This requires that each single point of damage be treated separately.

In U.S. Pat. No. 5,531,739 to Trelles, laser energy is delivered again from below the skin. The Trelles patent discloses a method in which laser energy is delivered via a fiber optic probe to a location underneath a blood vessel to be treated. The vessel is irradiated with a treatment beam having a fluence sufficient to coagulate and collapse the vessel at that location. Yet, again, this procedure must be repeated at multiple sites along the length of the blood vessel so that it will collapse along its length and no longer carry any blood.

In U.S. Pat. No. 5,053,033 to Clarke, laser energy is delivered endoluminally. The Clarke patent describes using laser energy in the range about 240 nanometers to about 280 nanometers delivered via an optical fiber or other waveguide incorporated, for example, into a percutaneous catheter. In operation, the ultraviolet laser energy kills smooth muscle cells at an angioplasty site, thereby reducing the risk of restenosis, while minimizing damage to surrounding tissue. However, this technique is used to keep a blood vessel open and, therefore, has little use in the treatment of varicose veins.

In U.S. Pat. No. 5,161,526 to Hellwing et al., laser energy in the wavelength range of 500 nanometers to 1100 nanometers is used. The Hellwing et al. patent describes using laser energy to aid in the treatment of hemophilia by biostimulating muscles and joints. However, this method delivers the laser energy from the surface of the skin. Thus, blood vessels in the treatment area remain unaffected.

In U.S. Pat. No. 5,707,403 to Grove et al., laser energy is used to affect blood vessels. In the Grove et al. patent, laser energy is delivered at the surface of the skin in the wavelength range 700 nanometers to 1100 nanometers. Blood vessels within the first 2 millimeters of the dermis can be treated with this method, otherwise the high fluence or energy can cause explosion of surface vessels and burning of the skin. Furthermore, the delivery of laser energy at the surface of the skin inevitably causes coagulation of blood within the blood vessel rather than causing fibrosis of the blood vessel itself.

Endovascular delivery of laser energy would decrease the amount of power necessary to treat the vein and virtually eliminate the potential for adverse side effects to the overlying skin and intervening tissues. In addition, fibrosis of the blood vessel is preferred because veins of a much larger diameter may therefore be treated safely and effectively.

Accordingly, a need exists for an endovascular laser treatment of varicose veins using laser energy in order to produce direct endothelial and vein wall damage with subsequent fibrosis.

SUMMARY OF THE INVENTION

It is an object of the present invention to improve the method of the treatment of varicose veins.

It is another object of the present invention to provide such a method that decreases varicose vein recurrence rates.

It is still another object of the present invention to provide such a method that causes direct endothelial and vein wall damage with subsequent fibrosis.

It is a further object of the present invention to provide such a method that introduces a fiber optic line into the vein lumen to deliver intraluminal laser energy with direct contact of the tip of the fiber optic line with the vein wall.

It is yet another object of the present invention to provide such a method that avoids blood clot formation and maximizes vein wall damage.

These and any other objects of the present invention are achieved by a method for treating varicose veins using a tipped laser energy carrier to deliver laser energy into the blood vessel lumen to produce direct endothelial and vein wall damage with subsequent fibrosis. By delivering laser energy intraluminally, the entire thickness of the vein wall is damaged. This results in fibrosis of the vein and a decrease in the diameter of the varicosity. Preferably, the vein wall will be damaged to the extent that the subsequent fibrosis causes the vein to collapse.

DETAILED DESCRIPTION OF THE INVENTION

Figure 1:
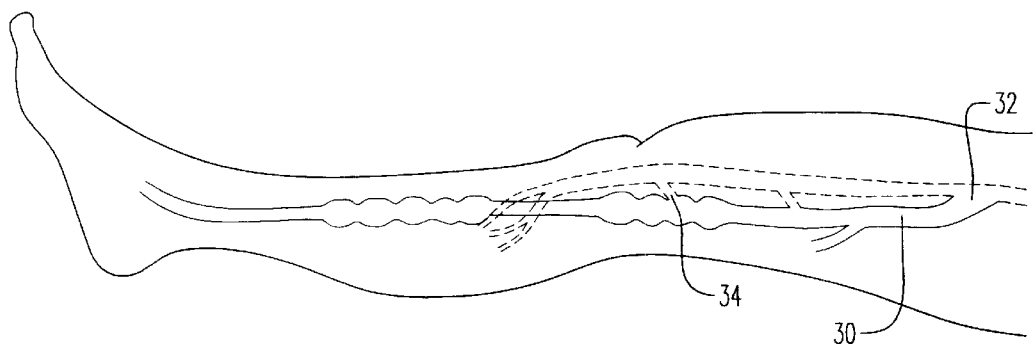
FIG. 1 is a lateral sectional view of a leg with varicose veins involving a greater saphenous vein.

Referring to the drawings and, in particular, FIG. 1, there is shown a leg generally represented by reference numeral 10. Leg 10 has a varicose, greater saphenous vein 30. A varicosity in greater saphenous vein is typically due to incompetence of the saphenofemoral valve with reflux at a saphenofemoral junction 32. Additional perforators 34 connect greater saphenous vein 30 to the deep venous system of leg 10.

The following is representative of methods of the present invention.

Figure 2:
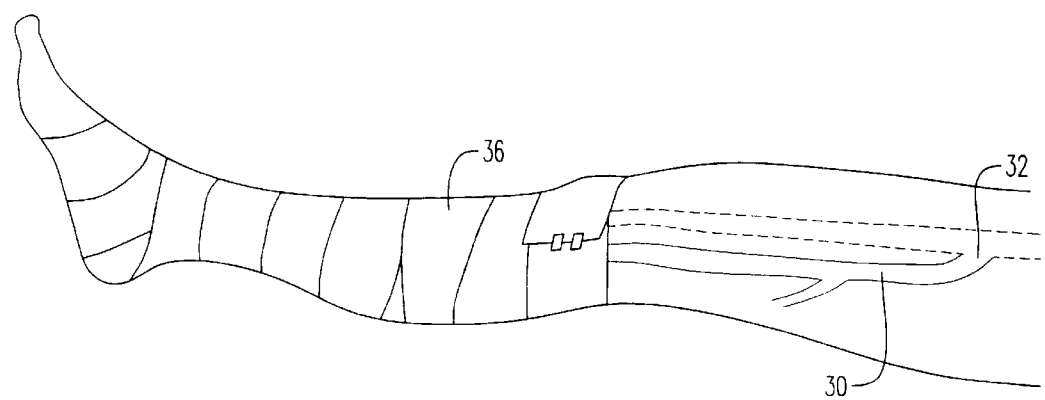
FIG. 2 shows application of a compression bandage to the leg of FIG. 1.

The treatment area is anesthetized following pre-procedure evaluation and informed consent. As shown in FIG. 2, a compression bandage 36 is applied starting from the distal end of the foot up to the planned entry site of an angiocatheter 38, shown in FIG. 3A. Compression bandage 36 facilitates emptying of the superficial venous system of leg 10.

Figure 3A:
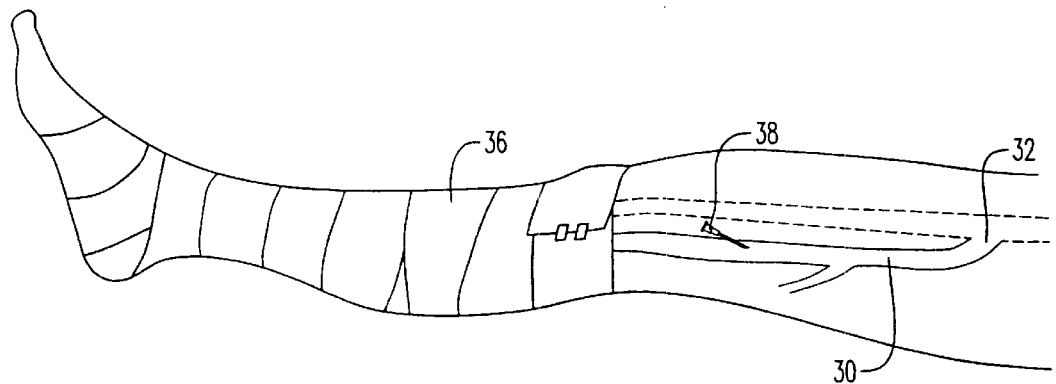
FIG. 3A shows percutaneous placement of an angiocatheter into the greater saphenous vein of the leg of FIG. 1.
Figure 3B:
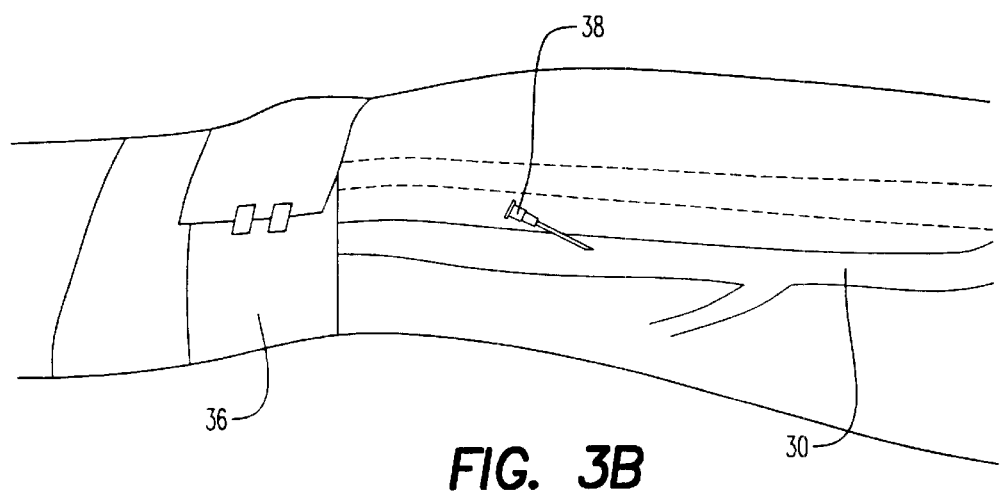
FIG. 3B shows an enlarged, detailed view of a portion of FIG. 3A.

As shown in FIGS. 3A and 3B, angiocatheter 38, or a device of similar function, is placed percutaneously into greater saphenous vein 30. To aid in the placement of angiocatheter 38, ultrasound imaging, or a similar functioning device, may be used.

As an alternative to the use of angiocatheter 38, an incision may be made above greater saphenous vein 30 at the planned entry site of a fiber optic line 40 so that the planned entry site may be visualized. Then, fiber optic line 40 can be inserted without the use of angiocatheter 38. However, use of angiocatheter 38 is preferred.

Figure 4A:
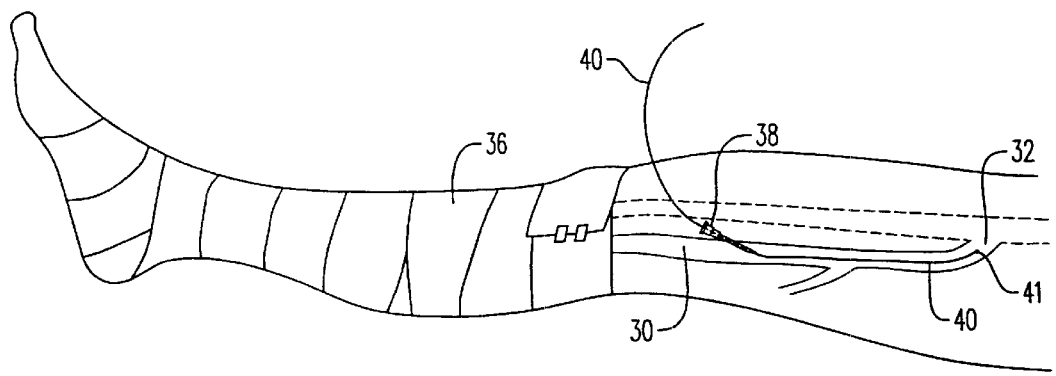
FIG. 4A shows endovascular placement of a tipped laser energy carrier into the greater saphenous vein of the leg of FIG. 1.
Figure 4B:
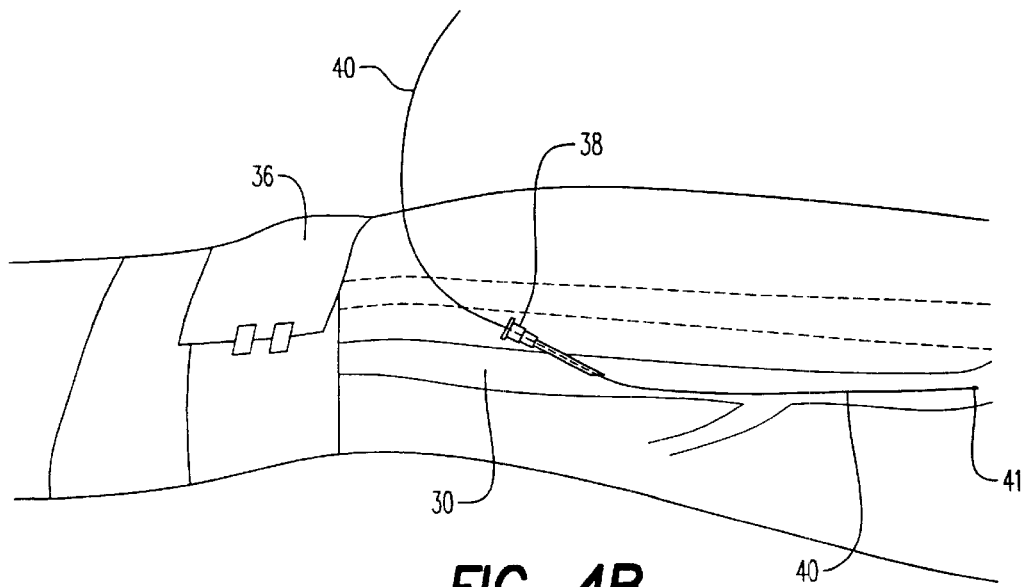
FIG. 4B shows an enlarged, detailed view of a portion of FIG. 4A.

Referring to FIGS. 4A and 4B, in a preferred embodiment, fiber optic line 40 is introduced into the vein lumen via angiocatheter 38. Fiber optic line 40 has a tip 41 that is uncoated so as to allow emittance of laser energy. The remainder of fiber optic line 40 can be coated with various substances known to the art. The coated portion of fiber optic line 40 will not emit laser energy. In addition, the coating provides fiber optic line 40 with a combination of flexibility and rigidity to minimizing the risk of breakage during manipulation. The tip of fiber optic line 40 is preferably rounded in shape, although other shapes are contemplated. A rounded tip 41 is preferred because it enables the operator to more easily control the amount of vein to be treated and decreases the risk of perforation of the vein during positioning of tip 41. Tip 41 preferably has an outer diameter about 200 microns to about 600 microns in diameter.

Figure 5:
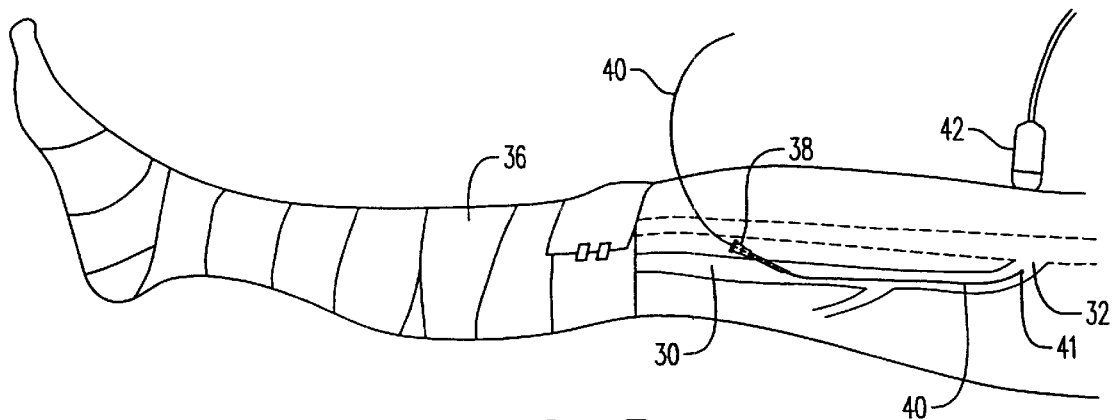
FIG. 5 shows a position of the tip of the laser energy carrier under ultrasound guidance in the leg of FIG. 1.

As illustrated in FIG. 5, tip 41 of fiber optic line 40 is positioned a few centimeters distal to the saphenofemoral junction 32. Positioning of tip 41 is preferably accomplished by emitting laser energy in the visible spectrum through tip 41. This visible spectrum energy can be seen through the skin and may be emitted concurrently with laser energy in other wavelengths. Alternatively, a traditional ultrasound imager, shown generally as 42, may be used.

Figure 6:
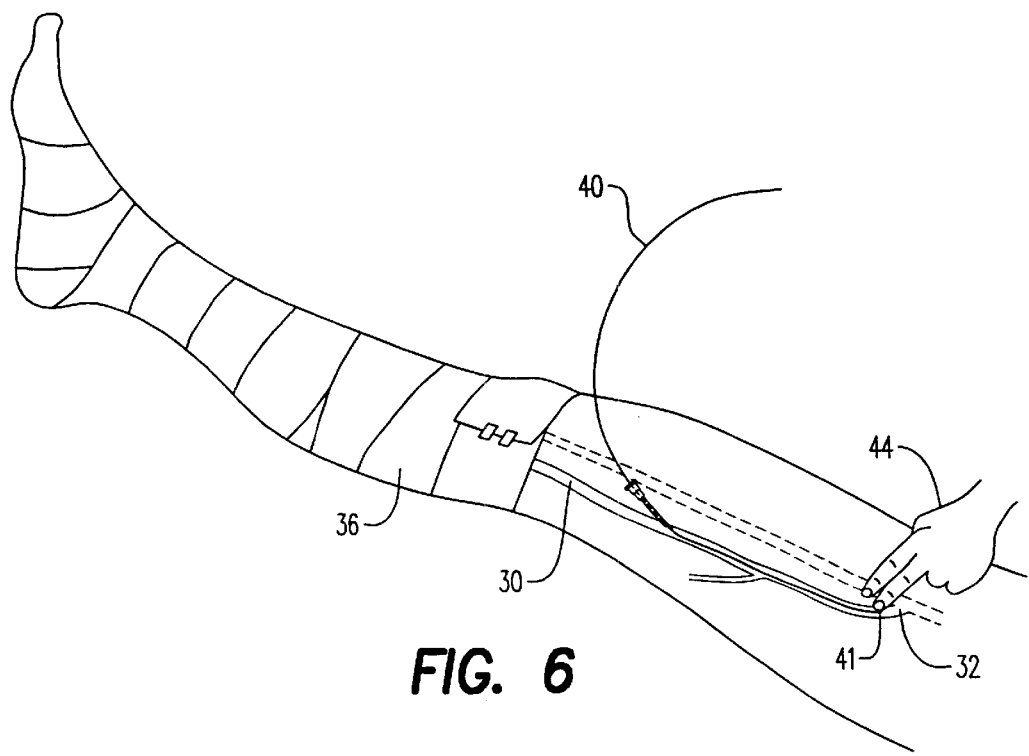
FIG. 6 shows removing of venous blood from the leg of FIG. 1 with elevation and manual compression at the saphenofemoral junction.

Then, the patient is placed in trendelenberg position or, as is shown in FIG. 6, leg 10 is elevated. In this position, saphenofemoral junction 32 is compressed, preferably by a hand 44 or ultrasound imager 42, to empty greater saphenous vein 30. An optional first compression bandage (not shown) may be applied to the upper portion of leg 10 to aid in keeping greater saphenous vein 30 empty of blood. After being emptied of blood, greater saphenous vein 30 is also compressed, preferably by hand 44 or by ultrasound imager 42, so that tip 41 of fiber optic line 40 makes direct contact with the vein wall. Then, laser energy about 500 nanometers to about 1100 nanometers in wavelength is delivered in bursts through fiber optic line 40 into the vein wall. Preferably, the laser energy is in the range from about 532 nanometers to about 1064 nanometers and the duration of each burst is about 0.2 seconds to about 10 seconds. Each burst delivers from about 5 to about 20 watts of energy into the vein wall. While laser energy is delivered in bursts through fiber optic line 40, the fiber optic line is incrementally withdrawn from greater saphenous vein 30. However, the compression of greater saphenous vein 30 around tip 41 is maintained as fiber optic line 40 is withdrawn. This method insures damage to the entire thickness of the vein wall of greater saphenous vein 30, ultimately resulting in fibrosis of the vein wall. Pibrosis of the vein wall leads to a decrease in the diameter of the vein. The amount of fibrosis in the vein wall is determined by the amount of laser energy delivered thereto. Preferably, the method will damage the vein wall to an extent that the subsequent fibrosis causes the vein to collapse. Alternatively, fibrosis of the vein wall will decrease the diameter of the vein such that normal unidirectional blood flow in greater saphenous vein 30 is restored.

Figure 7A:
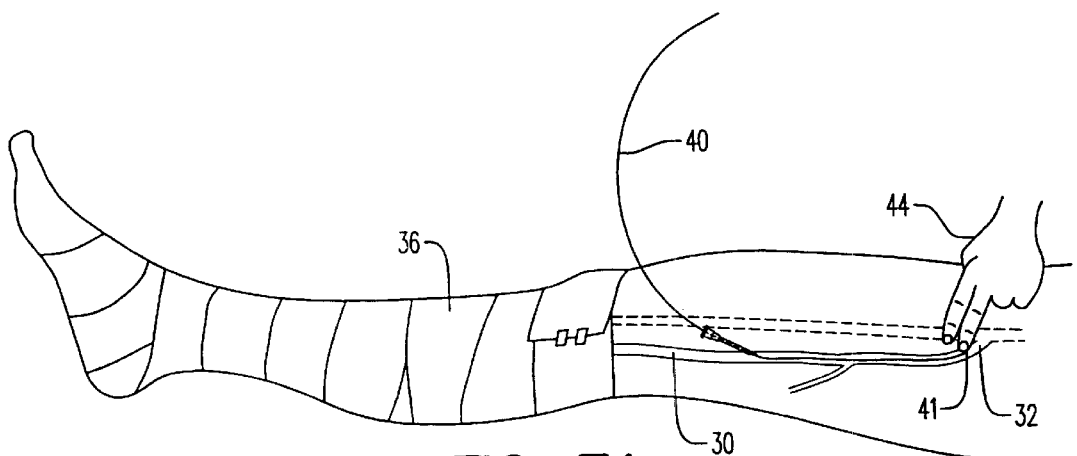
FIG. 7A shows manual finger compression over the tip of the fiber optic line during delivery of laser energy to the saphenofemoral junction of the greater saphenous vein of FIG. 1.
Figure 7B:
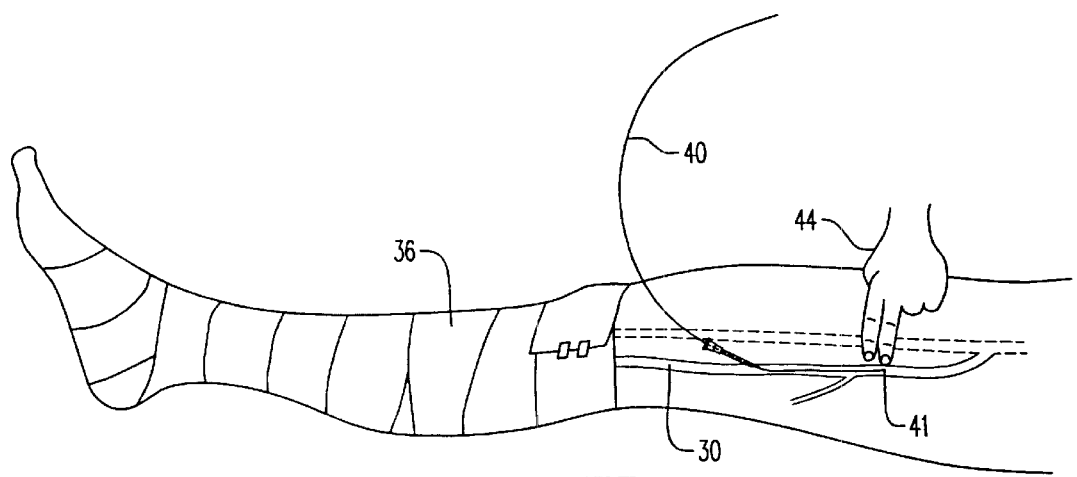
FIGS. 7B and 7C show manual finger compression over the tip of the fiber optic line while simultaneously delivering laser energy and withdrawing the fiber optic line from the greater saphenous vein of FIG. 1.
Figure 7C:
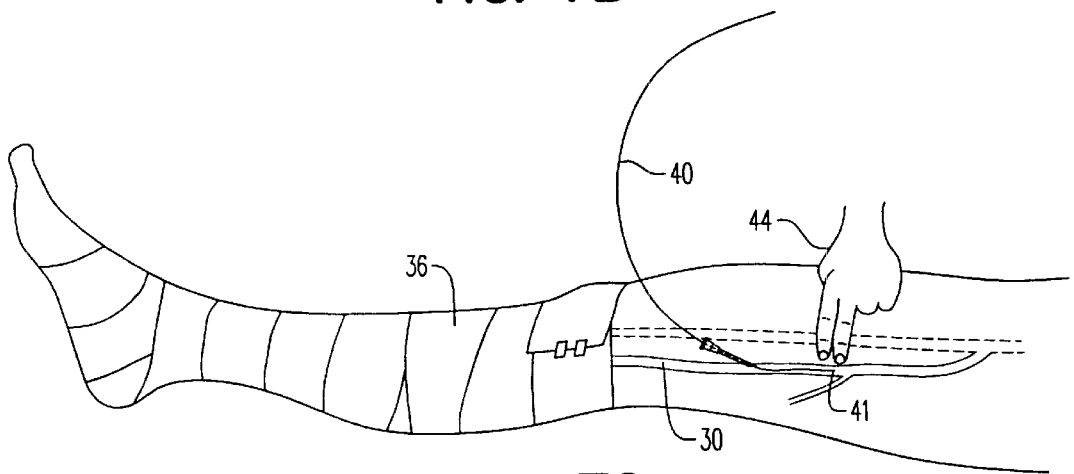

FIGS. 7A, 7B, and 7C illustrate three selected points of laser energy delivery with manual compression. Preferably, laser energy is first delivered to saphenofemoral junction 32 as shown in FIG. 7A. Beginning the treatment method as saphenofemoral junction 32 ensures that the entire length of greater saphenous vein 30 is treated with laser energy. Then, as shown in FIGS. 7B and 7C, compression is maintained over the tip of fiber optic line 40 as it simultaneously delivers laser energy to and is withdrawn from greater saphenous vein 30. The power and burst duration can be modified according to initial clinical observations and obtained results at the discretion of the provider. The range of power is set forth above.

Figure 8:
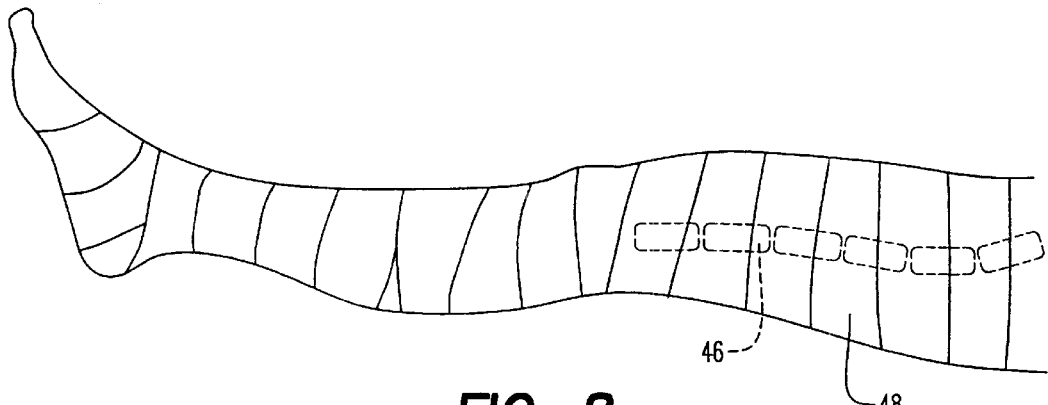
FIG. 8 shows an application of a compression bandage or stocking with foam pads along the course of the treated vein of the leg of FIG. 1.

As shown is FIG. 8, after fiber optic line 40 and angiocatheter 38 are removed, one or more foam pads, identified as 46, are used to cover the puncture site and the course of the treated vein. A second compression bandage or stocking 48 may be applied over foam pads 46.

Figure 9:
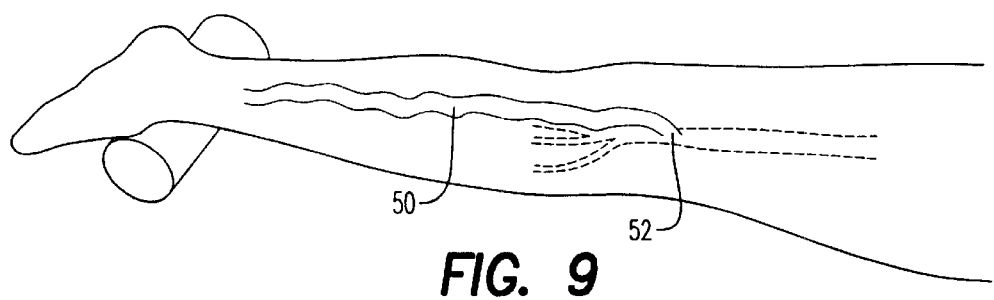
FIG. 9 shows a prone sectional view of a leg with varicose veins involving a lesser saphenous vein.
Figure 10:
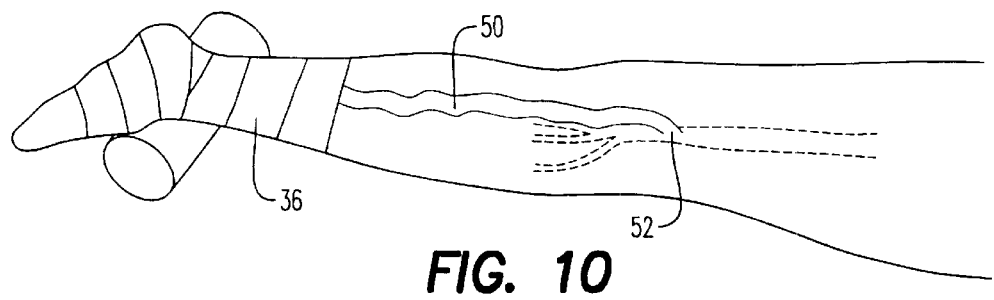
FIG. 10 shows an application of a compression bandage to the leg of FIG. 9.
Figure 11:
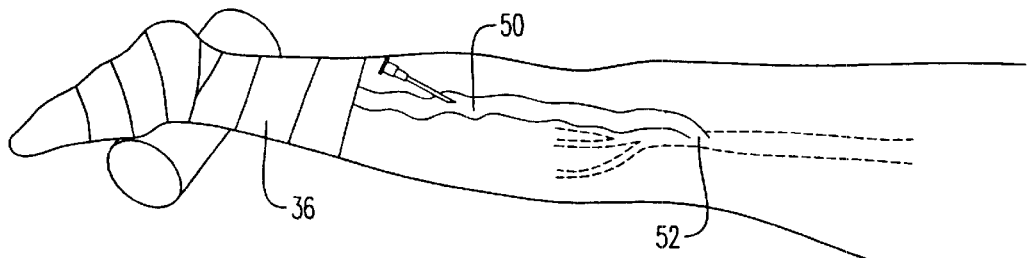
FIG. 11 shows percutaneous placement of an angiocatheter into the lesser saphenous vein of the leg of FIG. 9.
Figure 12:
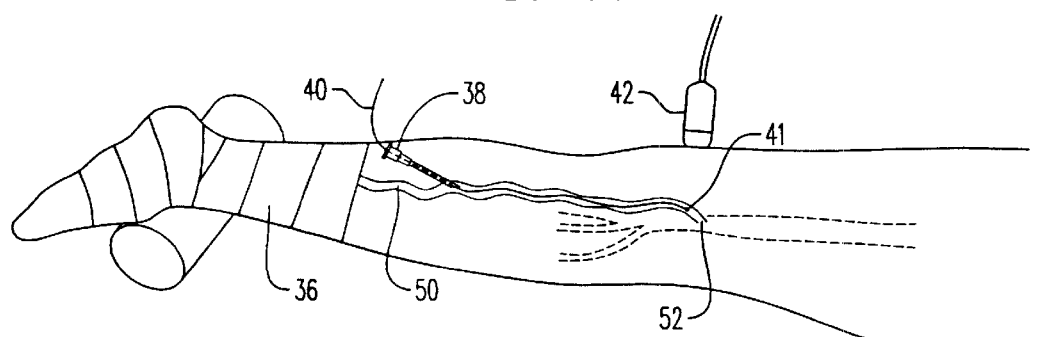
FIG. 12 shows positioning of the tip of a laser energy carrier under ultrasound guidance to the leg of FIG. 9.
Figure 13:
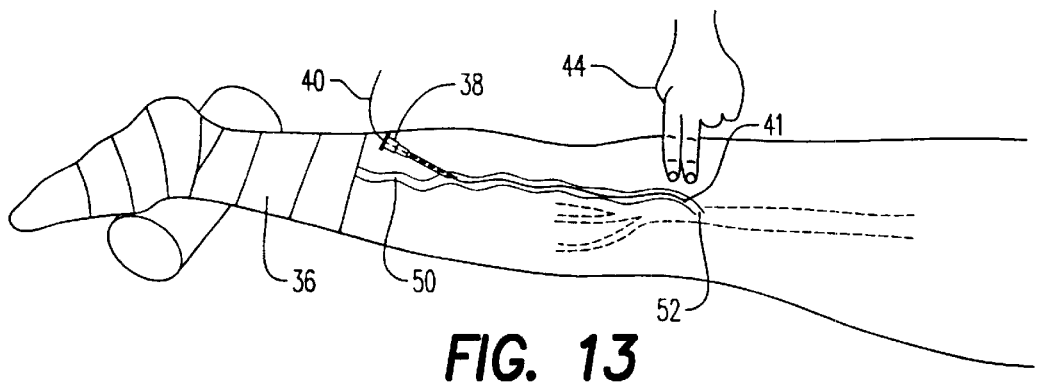
FIG. 13 shows a manual finger compression of the lesser saphenous vein at the tip of the laser energy carrier during delivery of laser energy to the leg of FIG. 9.

FIG. 9 shows a varicose, lesser saphenous vein 50. Such a varicosity is a typical consequence of the incompetence of saphenopopliteal valve 52 with reflux at the saphenopopliteal junction 52a. The procedure for treating lesser saphenous vein 50 is similar to the procedure used to treat greater saphenous vein 30. Thus, as stated above with reference to treatment of greater saphenous vein 30 and as now illustrated in FIG. 10, compression bandage 36 is applied to leg 10. Then, percutaneous access into lesser saphenous vein 50 is obtained with angiocatheter 38, or a similar functioning device, as shown in FIG. 11. Also as stated above with reference to treatment of greater saphenous vein 30 and as now illustrated in FIG. 12, fiber optic line 40 is placed into lesser saphenous vein 50 through angiocatheter 38. The fiber optic line 40 is positioned a few centimeters distal to saphenopopliteal junction 52. Again, visible spectrum energy emitted from tip 41, or ultrasound emitted from ultrasound imager 42, is preferably used to facilitate such precise placement. As illustrated in FIG. 13, leg 10 is then elevated and lesser saphenous vein 50 is drained of blood and compressed. The drainage of blood is important to insure direct contact of the vessel walls with tip 41 during delivery of laser energy. Again, the delivered laser energy is about 500 nanometers to about 1100 nanometers in wavelength, preferably about 532 nanometers to about 1064 nanometers, in bursts for about 0.2 seconds to about 10 seconds per burst for a total of about 5 watts to about 20 watts per burst. The above described procedure is followed, with compression of lesser saphenous vein 50 maintained around tip 41, while fiber optic line 40 is incrementally withdrawn.

Figure 14:
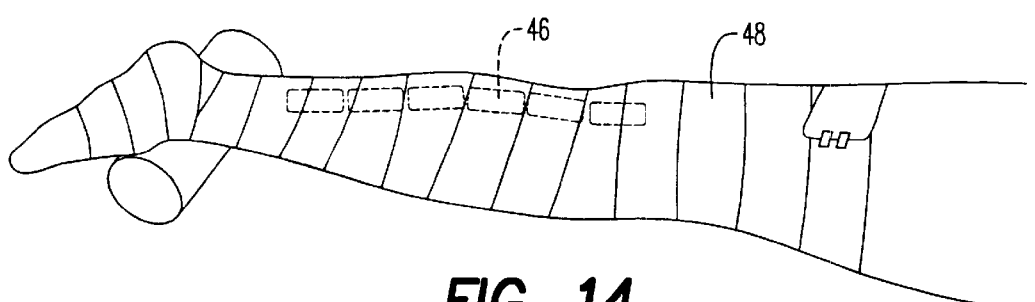
FIG. 14 shows an application of a compression bandage or stocking with foam pads along the course of the treated vein in the leg of FIG. 9.

FIG. 14 shows that foam pads 46 are applied at the puncture site and along the treated vein after fiber optic line 40 is completely withdrawn. A second compression bandage or stocking 48 may then be applied over foam pads 46.

Figure 15:
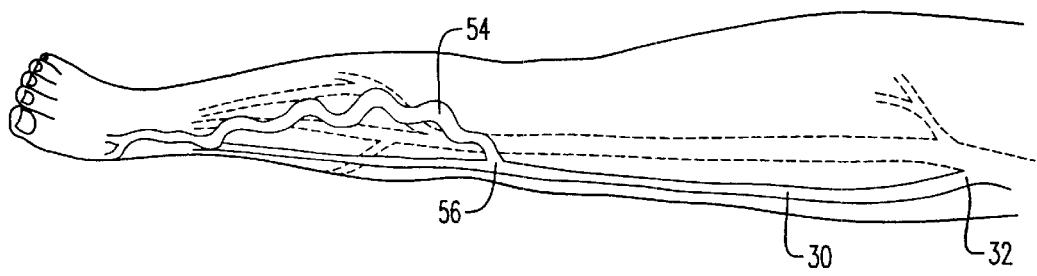
FIG. 15 shows a supine sectional view of a leg with varicose veins with isolated perforator incompetence.
Figure 16:
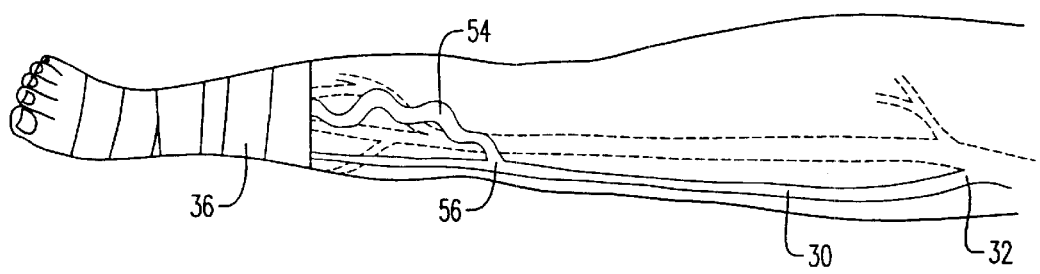
FIG. 16 shows application of a compression bandage to the leg of FIG. 15.
Figure 17:
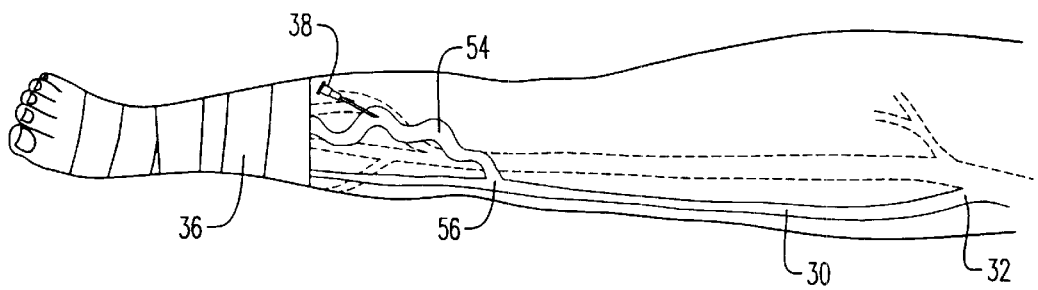
FIG. 17 shows percutaneous placement of an angiocatheter into the varicose vein of the leg of FIG. 15.
Figure 18:
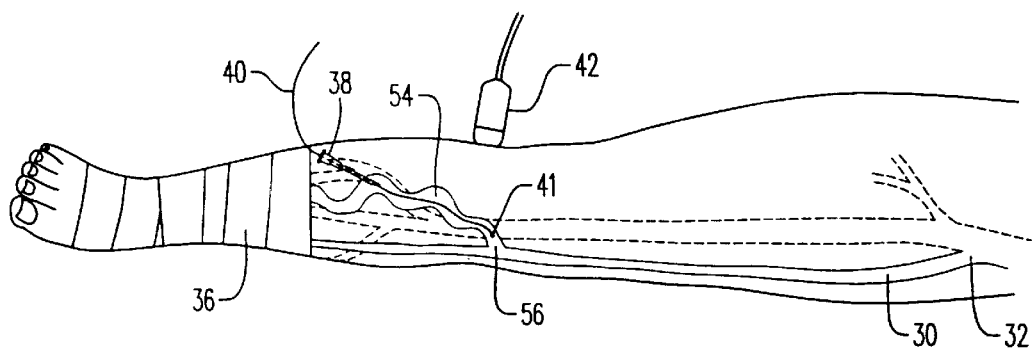
FIG. 18 shows positioning of the tip of a laser energy carrier under ultrasound guidance to the leg of FIG. 15.
Figure 19:
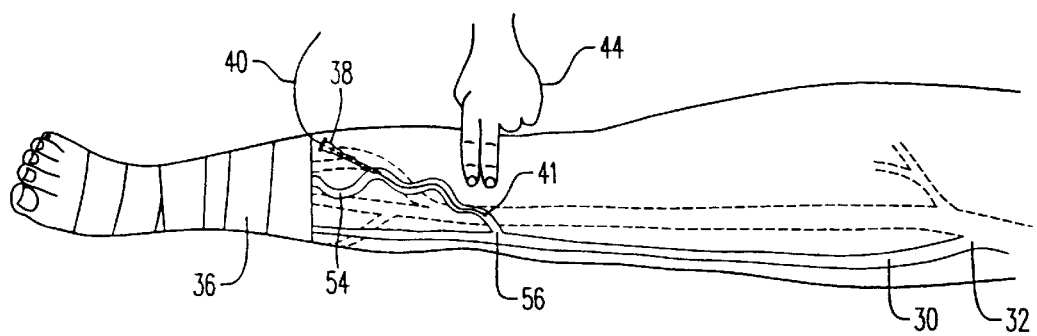
FIG. 19 shows a manual finger compression of the varicose vein of the leg of FIG. 15 at the tip of the laser energy carrier during delivery of laser energy.

Another example of a vein, identified generally as 54, having a varicosity that can be treated with the described endovascular laser method is illustrated in FIG. 15. The varicosity in vein 54 is due to an isolated perforator incompetence, which creates a point of refluM 56 even though the saphenofemoral junction 32 remains intact. The procedure for treating vein 54 is similar to the procedure for treating both greater and lesser saphenous veins 30 and 50. As now illustrated in FIG. 16, first compression bandage 36 is applied to leg 10, then percutaneous access into vein 54 is obtained with angiocatheter 38, or a device of similar function, as shown in FIG. 17. Referring to FIG. 18, fiber optic line 40 is then placed into vein 54 through angiocatheter 38 and positioned a few centimeters distal to point of reflux 56 by using visible spectrum energy emitted from tip 41 or by using another instrument, such as ultrasound imager 42. As shown in FIG. 19, leg 10 is elevated. Then, vein 54 is emptied of blood and compressed to insure direct contact of the vessel walls with tip 41 during delivery of laser energy. Again, laser energy is delivered at about 500 nanometers to about 1100 nanometers in wavelength, preferably about 532 nanometers to about 1064 nanometers, for bursts about 0.2 seconds to about 10 seconds per burst, for a total of about 5 watts to about 20 watts per burst. The above described procedure continues to be followed as the process of compression of vein 54 around tip 41 is repeated while fiber optic line 40 is withdrawn.

Figure 20:
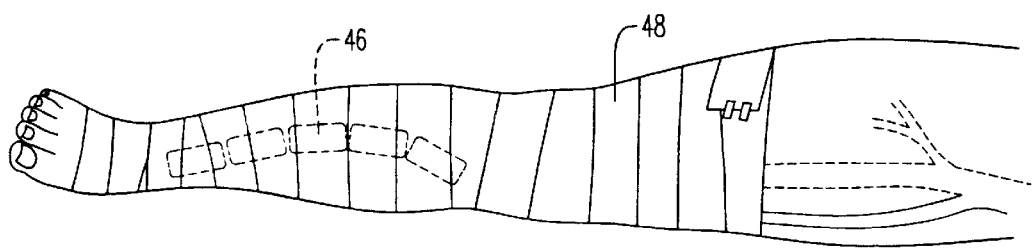
FIG. 20 shows an application of a compression bandage or stocking with foam pads along the course of the treated vein of the leg of FIG. 15.

Again, FIG. 20 shows that foam pads 46 are applied at the puncture site and along the treated vein, and then a second compression bandage or stocking 48 may be applied over foam pads 46.

Varicose veins in other locations can be treated with similar endovascular laser techniques.

Although the description above contains specificities, these should not be construed as limiting the scope of the present invention, but as merely providing illustrations of some of the presently preferred embodiments of the present invention.

The present invention having thus been described with particular reference to the preferred forms thereof, it will be obvious that various changes and modifications may be made therein without departing from the spirit and scope of the present invention as defined in the appended claims.

What we claim is:

1. A blood vessel treatment device comprising:
   means adapted for insertion into a blood vessel; and
   means adapted for intraluminal contact with a wall of said blood vessel, for emitting laser energy to cause a decrease in the diameter of said blood vessel.

2. The blood vessel treatment device of claim 1, wherein said laser energy causes said blood vessel to collapse.

3. The blood vessel treatment device of claim 1, wherein said emitting means is about 200 microns to about 600 microns in diameter.

4. The blood vessel treatment device of claim 1, wherein said emitting means is a fiber optic line.

5. The blood vessel treatment device of claim 1, wherein said emitting means has a laser emitting section located at a tip of said emitting means.

6. The blood vessel treatment device of claim 5, wherein said tip of said emitting means is rounded.

7. The blood vessel treatment device of claim 1, wherein said laser energy is applied in the range about 500 nanometers to about 1100 nanometers.

8. The blood vessel treatment device of claim 1, wherein said laser energy is delivered in bursts.

9. A method of treating a blood vessel using laser energy, comprising the steps of:
   inserting means for emitting laser energy into the blood vessel at a puncture site, wherein said emitting means has a laser emitting section;
   placing said laser emitting section of said emitting means into intraluminal contact with the blood vessel at a treatment site; and
   emitting said laser energy into the blood vessel through said laser emitting section of said emitting means, thereby decreasing the diameter of said blood vessel.

10. The method of claim 9, further comprising emptying the blood vessel prior to emitting said laser energy.

11. The method of claim 9, wherein said emitting means is inserted into the blood vessel through the use of an angiocatheter.

12. The method of claim 9, wherein said emitting means is about 200 microns to about 600 microns in diameter.

13. The method of claim 9, wherein said emitting means is a fiber optic line.

14. The method of claim 9, wherein said laser emitting section of said emitting means is located at a tip of said emitting means.

15. The method of claim 14, wherein said tip of said emitting means is rounded.

16. The method of claim 14, wherein said tip of said emitting means is located at the treatment site through the use of a guidance means.

17. The method of claim 9, further comprising applying compression externally to the blood vessel prior to applying said laser energy, thereby ensuring contact of said tip of said emitting means with the blood vessel.

18. The method of claim 9, wherein said laser energy is applied in the range of about 500 nanometers to about 1100 nanometers.

19. The method of claim 9, wherein said laser energy is delivered in bursts.

20. The method of claim 9, further comprising:
   removing said emitting means after applying said laser energy;
   placing foam pads over said puncture site;
   placing foam pads over the blood vessel; and
   applying a compression means over said foam pads.

21. A method of treating a blood vessel using laser energy, comprising the steps of:
   inserting means for emitting laser energy into the blood vessel at a puncture site, wherein said emitting means has a laser emitting section;
   placing said laser emitting section of said emitting means into intraluminal contact with the blood vessel at a treatment site;
   emptying the blood vessel; and
   emitting said laser energy into the blood vessel through said laser emitting section of said emitting means, thereby decreasing the diameter of said blood vessel.

* * * * *

UNITED STATES PATENT AND TRADEMARK OFFICE
CERTIFICATE OF CORRECTION

PATENT NO. : 6,398,777 B1
DATED : June 4, 2002
INVENTOR(S) : Luis Navarro et al.

It is certified that error appears in the above-identified patent and that said Letters Patent is hereby corrected as shown below:

<u>Title page,</u>
Insert Item:
      -- Related U.S. Application Data

[62] Provisional Application No. 60/119,235, filed on February 9, 1999; Provisional Application No. 60/118,050, filed on February 1, 1999. --

Signed and Sealed this

Twenty-ninth Day of April, 2003

JAMES E. ROGAN
*Director of the United States Patent and Trademark Office*